United States Patent [19]
Magram

[11] Patent Number: 5,902,254
[45] Date of Patent: May 11, 1999

[54] CATHETHER GUIDEWIRE

[75] Inventor: Gary Magram, Baltimore, Md.

[73] Assignee: The Nemours Foundation, Jacksonville, Fla.

[21] Appl. No.: 08/681,707

[22] Filed: Jul. 29, 1996

[51] Int. Cl.⁶ ................................................. A61B 5/00
[52] U.S. Cl. .............................................................. 600/585
[58] Field of Search ...................................... 128/657, 658, 128/772; 604/95, 280, 282; 600/137, 139, 141, 142, 144, 146, 434, 435, 585

[56] References Cited

U.S. PATENT DOCUMENTS

| | | | |
|---|---|---|---|
| 3,058,473 | 10/1962 | Whitehead | 604/95 |
| 3,674,014 | 7/1972 | Tillander . | |
| 3,913,565 | 10/1975 | Kawahara | 128/772 |
| 4,054,128 | 10/1977 | Seufert et al. | 600/141 |
| 4,111,190 | 9/1978 | Plumridge | 128/658 |
| 4,884,579 | 12/1989 | Engelson | 128/772 |
| 5,095,915 | 3/1992 | Engelson | 128/772 |
| 5,120,308 | 6/1992 | Hess | 604/95 |
| 5,234,003 | 8/1993 | Hall | 128/772 |
| 5,243,996 | 9/1993 | Hall | 128/772 |
| 5,299,580 | 4/1994 | Atkinson et al. | 128/772 |
| 5,365,942 | 11/1994 | Shank | 128/772 |
| 5,368,049 | 11/1994 | Raman et al. | 128/772 |
| 5,385,152 | 1/1995 | Abele et al. | 128/772 |
| 5,402,799 | 4/1995 | Colon et al. | 128/772 |
| 5,497,785 | 3/1996 | Viera | 128/772 |

Primary Examiner—Max Hindenburg
Attorney, Agent, or Firm—J. Michael Martinez de Andino; McGuire, Woods, Battle & Boothe LLP; Jeffrey C. Lew

[57] ABSTRACT

A guidewire useful for feeding a medical catheter through a body duct network to a distant target site within the body has a flexible distal portion. The distal portion facilitates threading the guidewire in a tortuous path through acute bends at branch junctions in the duct network. The guidewire end is able to feed into very delicate vessels such as ventricles of the brain and the spinal canal without puncturing the walls or damaging organs.

The novel guidewire includes beads displaced longitudinally at the distal end of a core wire. The beads are separated by a gap distance. The core wire can flex at points within the gaps between beads which allows the dial end of the guidewire to bend at branch junctions and to conform to the curvature in the vessel duct. The beads can be fixed to the core wire or they can move freely along the distal portion. Also, beads freely sliding along the core wire can be compressed against each other to control the degrees of stiffness and curvature of the distal portion by manipulating the proximal end of the guidewire outside the body during deployment of the guidewire. An insertion tube is provided for initially feeding the flexible guidewire end into the body duct.

16 Claims, 7 Drawing Sheets

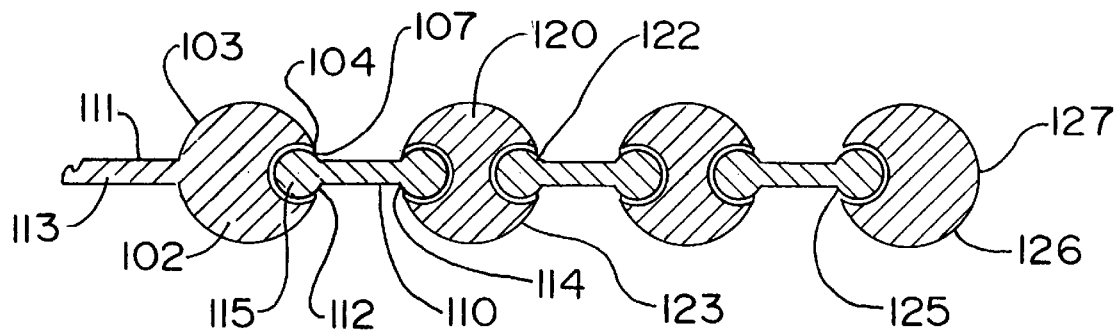
FIG. 9
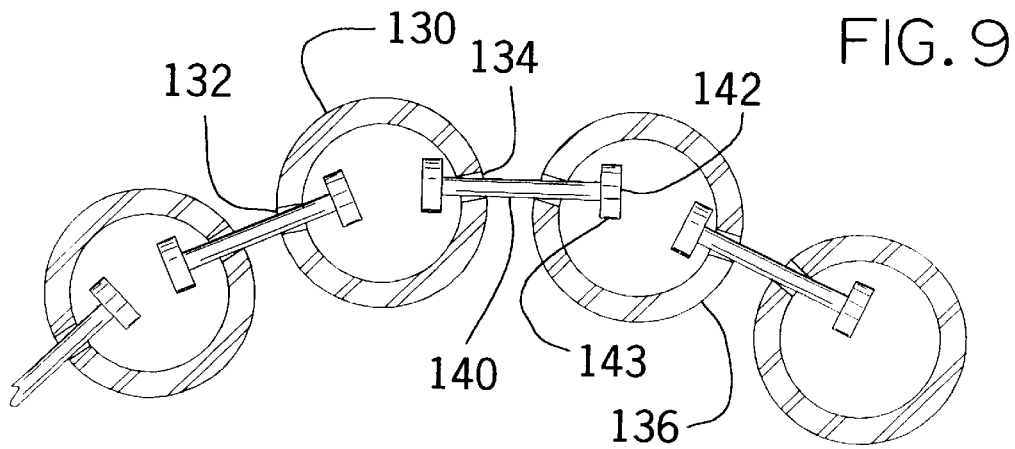
FIG. 10
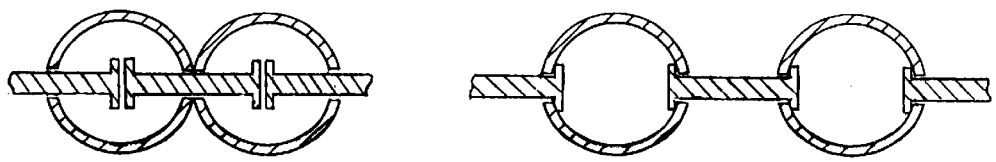
FIG. 11
FIG. 12

5,902,254

CATHETHER GUIDEWIRE

FIELD OF THE INVENTION

This invention relates to a guidewire used to deploy medical catheters in ducts within the body. More specifically, it relates to guidewires for use in ventricles of the brain or in the spinal canal.

Catheters are used to perform various diagnostic and therapeutic procedures at selected sites within animal, and especially human bodies. In such procedures it is desired to position the operative portion of the catheter at a target location in a blood vessel, brain or spinal cavity, or other body duct distant from the point of catheter entry. For example, one of the increasingly common types of catheterization procedures is percutaneous transluminal coronary angioplasty ("PITCA"). Greatly simplified, PTCA involves opening a coronary artery which has become partially blocked by plaque deposits to increase blood flow. It is accomplished by repeatedly inflating and deflating a balloon in the lumen of the artery at the location of the partial occlusion. The deflated balloon is delivered to the occluded site by a specially designed catheter which is inserted through an incision usually in the femoral artery. PTCA is sometimes accompanied by deploying a generally tubular, reinforcement stent in the opened artery to shore up weakened, blood vessel walls. The stent is also delivered to the site by a catheter designed for that purpose.

Several aspects of physiology make catheter deployment difficult. For one, the distance between the catheter entrance point and the target site is often considerable. Additionally, the body has a highly branched vessel network between the incision point and the target site. The size of the lumen of the vessels leading to the target site is normally quite small. Hence the path which the catheter must follow is narrow and tortuous.

To facilitate catheterization, a guidewire is often employed to direct the catheter toward the desired location. The guidewire is typically inserted through the incision before the catheter. The proximal end which remains outside the body is manipulated to urge the guidewire along the vessel network. Guidewires are commonly constructed from radio-opaque materials, and therefore, various methods such as X-ray fluoroscopy are available to monitor progress of the guidewire along the path. When the guidewire reaches the intended destination, the catheter cam be slipped over the proximal end and threaded along the guidewire to the target. The guidewire, then residing within the lumen of the catheter, can be withdrawn through the incision leaving the catheter in position to carry out the desired procedure.

Catheter guidewires are subject to significant structural design constraints. They are quite slender in order to fit into small ducts while leaving room for the catheter to slide over the guidewire inside the duct. The diameter of PTCA guidewires, for example, is generally less than about 0.5 mm (0.02 inches). The guidewire should also have adequate torsional strength over its full length to permit steering the distal portion into the correct vessel branches by axially rotating the proximal end. The guidewire, and especially the distal portion, should be sufficiently flexible that it can conform to the acute curvature of the vessel network. Additionally, the guidewire should have compressive strength suitable to push the wire into the vessel without folding back on itself. Also, the tip of the guidewire importantly should be adapted to avoid puncturing or otherwise damaging delicate vessel was and body tissue.

Various guidewire designs have been developed to satisfy these rigorous requirements. Often such designs include a core wire with a cross section which reduces progressively toward the tip to make the leading end very flexible. One very popular guidewire design enhancement is a leading end which incorporates a helical coil of fine diameter wire. Frequently, the helical coil is wound about the core. Helical coil-tipped catheter guidewires are disclosed in U.S. Pat. Nos. 4,884,579; 5,120,308; 5,234,003; 5,243,996; 5,365,942; 5,368,049; and 5,402,799, for example.

In neurosurgery, it is occasionally desirable to deploy a catheter in a ventricle of the brain or in the spinal canal. Conventional guidewires, including helical coil-tipped guidewires, are generally unsuitable because the tips are normally springy and stiff enough to easily puncture the extremely delicate tissue of the ducts being probed. Damage to the brain or the spinal cord resulting from unintentional guidewire wounds can be quite severe. A traditional guidewire tip which is made sufficiently soft to reduce the risk of tissue penetration, is usually too flexible. It lacks stiffness and consequently tends to buckle in the needle used to feed the guidewire or in the duct. Thus there exists a need for a neurosurgical catheter guidewire which can advance through a tortuous path and which has an especially gentle leading end.

Accordingly, it is an object of the present invention to provide a guidewire for facilitating the deployment of catheters in vessels and ducts within the body.

It is another object of this invention to provide a catheter guidewire with an extremely flexible tip and which can be threaded along a tortuous path with reduced risk of puncturing delicate tissue of the walls of ducts and vessels being probed.

It is still another object of this invention to provide a neurosurgical catheter guidewire which is suitable for assisting the deployment of a catheter in a ventricle of the brain or in the spinal canal.

Yet another object of this invention is to provide a neurosurgical catheter guidewire which can be advanced into a ventricle of the brain or the intradural sac with diminished exposure to injury of the brain tissue or spinal cord, respectively.

A still further object of this invention has to provide an improved guidewire for use in deploying catheters in various vessels, ducts and organs within the body, including vascular, digestive, urinary, and reproductive systems.

BRIEF DESCRIPTION OF THE DRAWINGS

FIG. 9 is a partial section view of the distal portion constructed of ball and post members, according to the present invention.

FIG. 10 is a section view of a part of a different embodiment of a ball and post member distal portion.

FIG. 11 is a section view of part of the distal portion of the guidewire of FIG. 10 wherein adjacent balls are in contact.

FIG. 12 is a section view of part of the distal portion of the guidewire of FIG. 10 wherein adjacent balls are separated by a full post member length.

DETAILED DESCRIPTION

Figure 1:
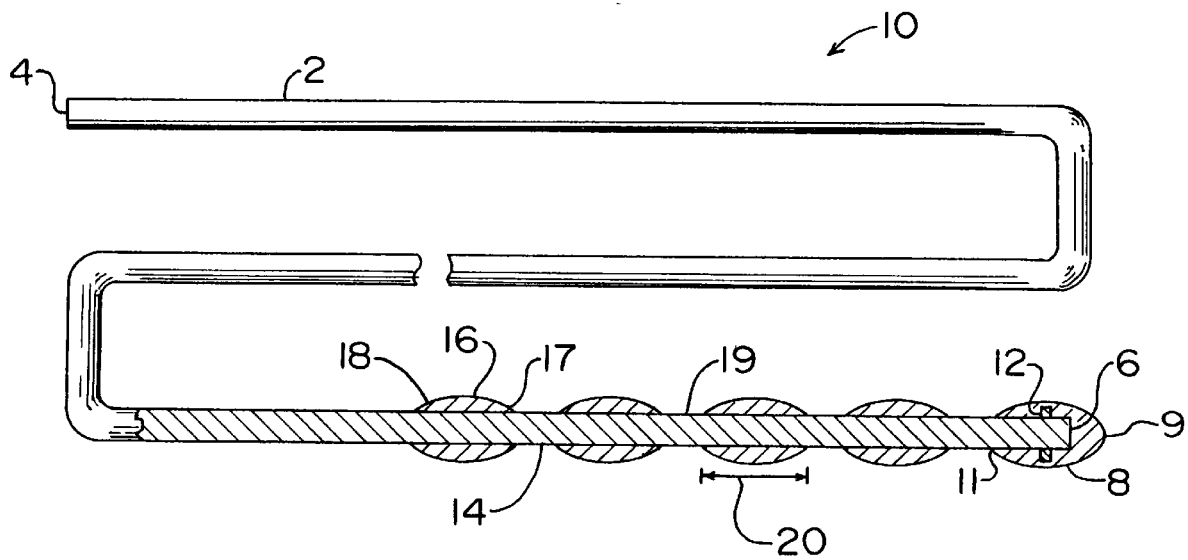
FIG. 1 is a partial section view of a guidewire according to the present invention wherein beads are fixed to the distal portion.

A first embodiment of the invention can be understood with reference to FIG. 1. The catheter guidewire 10 has a slender core wire 2 of sufficient length to reach a distant target site when fed percutaneously from a point outside the body into the lumen of a bodily duct. Mostly, overall length of the core wire is about 50–300 cm. The guidewire has a proximal end 4 which remains outside the body and is manipulated by the physician. Generally, the core wire is flexible so as to be capable of threading through a branched bodily duct network along a tortuous path. The thickness, shape of cross section and materials of construction of the core wire can vary along the length to provide different mechanical properties, such as flexibility and torsional strength. Normally, the core wire near the proximal end can be relatively stiff. This portion of the guidewire can be less flexible because it usually resides in larger diameter, slightly curving sections of the duct network near the entry point. For example, PTCA catheter guidewires are usually inserted in the femoral artery near the groin. Also the increased stiffness near the proximal end facilitates transmission of torque along the full length of the guidewire to steer the tip at the distal end. Generally, guidewire flexibility increases along the length toward the distal end.

Throughout this specification reference will be made to the cross section dimension of particular articles which may have noncircular or circular cross sections. For example, the core wire preferably has a circular cross section, although other cross section shapes can be useful. Unless otherwise stated, the term "diameter" herein shall mean the maximum cross section dimension, i.e. the diameter of a circumscribing circle of a noncircular cross section shape as well as the true diameter of a circular cross section. The diameter of the core wire over the proximal portion of the guidewire can generally taper in the axial direction from the proximal end to the distal end. This geometry permits the guide wire to slide easily into the duct lumen which normally becomes progressively smaller approaching the target site. However, the core wire diameter should remain sufficiently large that the proximal portion can adequately transit axial and torsional manipulative forces from the proximal end along the full length, which can be a considerable distance. The diameter of the proximal portion of the guidewire can be about 0.1 to about 2 mm.

At its distal end the core wire terminates at tip 6 on which is affixed a head 8. Because the head leads the guidewire through the bodily duct, the forward end 9 is blunt to reduce the risk that the head will puncture a delicate wall of the duct if the guidewire is inserted with slightly excessive force. The head can have a conical or spheroidal shape. The term "spheroidal" means that the shape can be imperfectly spherical as well as exactly spherical. Spheroidal shapes include spherical, elliptical, oval and hemi-spheroidally-ended, cylindrical shapes. If conical, the forward and trailing ends should be blunted to elate sharp edges that can gouge or penetrate the duct walls. That is, the cone should have an aerodynamic "nose cone" appearance. A preferred head is egg-shaped, i.e., an asymmetrical oval with the forward end 9 having a smaller diameter than the trailing end 11.

To assure that the head does not separate from the core wire, the head should be securely attached to the tip. The method of attachment is not critical to operation of the invention. For example, the head and core wire can be fabricated as a single piece, the head thus being integral to the core. Alternative exemplary methods of attachment include cementing, thermally fusing or crimping the head to the core wire, fastening with clamps, pins and set screws, and any combination of these. In FIG. 1 the tip of the core wire is shown to penetrate plate 12, seen in cross section, which is embedded in the head. The tip can be adhered to the plate by conventional methods to anchor the head to the wire.

The distal portion 14 includes a plurality of spheroidal beads 16 positioned sequentially along the core wire. The beads are also securely attached to the wire. Any of the previously stated methods for attaching the head to the wire can also be used for the spheroidal beads. The beads generally have smooth, rounded surfaces to prevent drag against the duct walls during guidewire movement within the duct lumen. The leading end 17 and trailing end 18 of the bead are both rounded to facilitate movement of the guidewire in the reverse as well as forward axial direction. Preferably the beads are axially symmetrical, meaning that the curvature of the leading and trailing ends is the same. The rounded nature of the leading and trailing ends also assists the core wire to flex smoothly in regions between the beads. By flexing smoothly, the distal portion is able to assume curvature of continuously variable radius and to resist kinking or jamming when being fed into the duct. Representative bead shapes include spherical, elliptical, oval and cylindrical, i.e., cylindrical beads having hemi-spheroidal ends. Spherical and elliptical bead shape is preferred.

The distal portion of the guidewire is intended to lead the guidewire into the usually very small duct branches in the far reaches of the network. Consequently, the diameter of the beads should be sufficiently small for the distal portion to slide easily through the narrowest ducts. Therefore, the diameter of the beads in the direction perpendicular to the core wire axis should be at most about 1.5 mm.

Figure 2A:
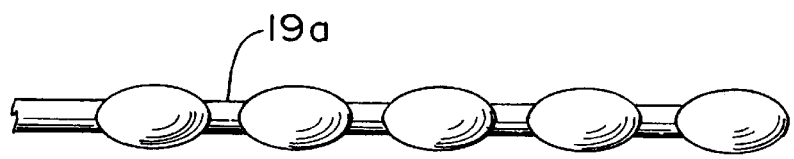
FIGS. 2a, 2b, and 2c are side views of the distal portion of a guidewire of this invention wherein the bead spacing as moderate, small and large, respectively.
Figure 2B:
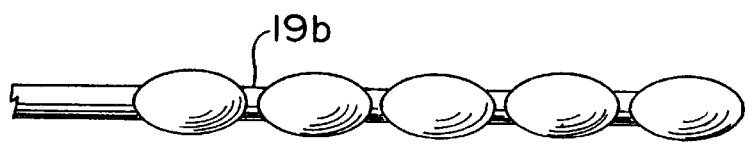
Figure 2C:
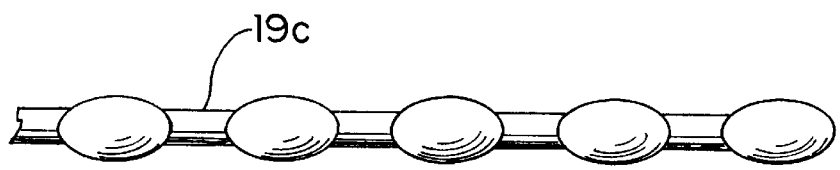
Figure 3A:
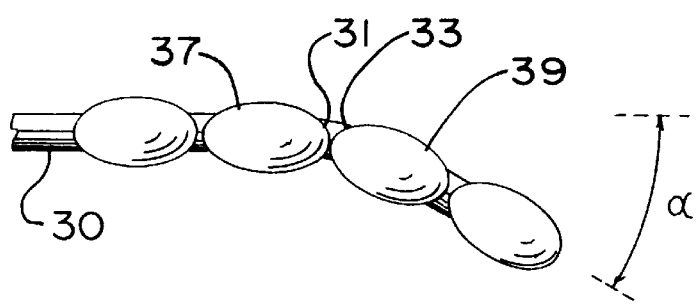
FIGS. 3a, 3b and 3c illustrate the maximum angles of deflection between adjacent beads spaced apart as in FIGS. 2a, 2b, and 2c, respectively.
Figure 3B:
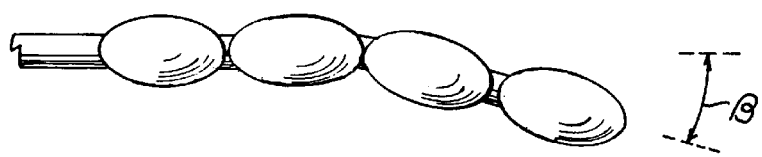
Figure 3C:
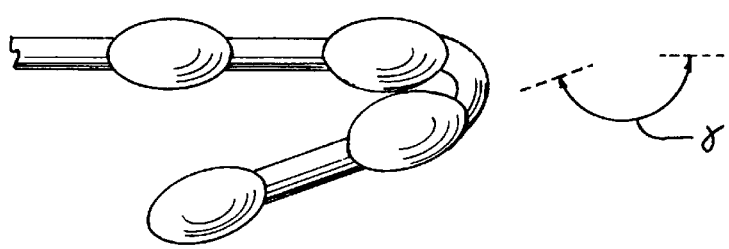
Figure 3D:
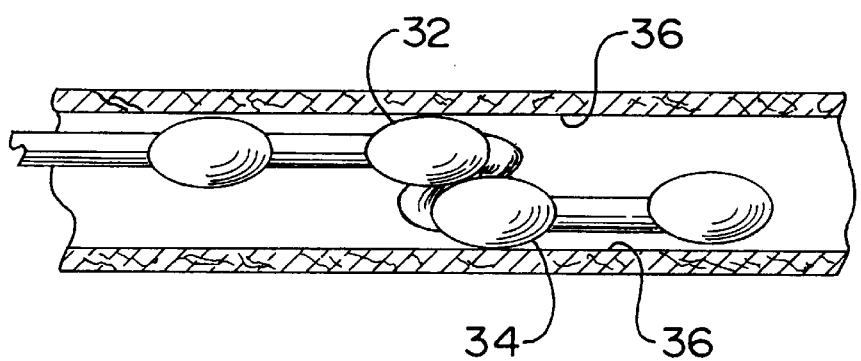
FIG. 3d is a section view of bodily duct in which a guidewire with large bead spacing is jammed.

The beads are spaced apart along the axis of the core wire by a small distance which creates a gap 19 between adjacent beads. The core wire can flex freely in the gaps. Such flexing permits the distal portion to assume suitable curvature to advance the distal end toward the target site through acute curves in the narrow duct network. If the distal portion is too flexible, it tends to kink and jam. The size of the gap distance in relation to the bead and lumen dimensions is important for defining the minimum radius of curvature and the tendency of the distal end to kink or jam. For example, FIGS. 2a, 2b and 2c illustrate a section of the distal portion of the guidewire of FIG. 1 in which the gap distances 19a, 19b and 19c, between adjacent, identically sized, beads are medium, small and large, respectively. FIGS. 3a, 3b and 3c show the distal portions of FIGS. 2a–2c, respectively, in the flexed state. As seen in FIG. 3a, the core wire 30 is free to flex until the leading end 31 of proximal bead 37 contacts the trading end 33 of the adjacent distal bead 39 to define an angle of deflection, α. By increasing axial thrust applied from the proximal portion of the guidewire, the beads can be forced to pivot against each other at the point of contact. This pivoting can cause the deflection angle to increase slightly as the core wire curvature between the beads stretches to its limit. If the gap distance is small, as in FIG. 3b, the leading and trailing ends contact ache other when the core has flexed to only a small deflection angle β. Such a distal portion will not be able to bend around sharp curves. FIG. 3c shows that adjacent beads can deflect to an angle γ of more than 90° if the gap distance is very large. If the core wire is permitted to flex to too great an angle, the distal portion can fold onto itself inside the duct causing the guidewire to kink. Furthermore, if the gap distance is too large, a following bead 32 can overtake a leading bead 34 to cause a jam against the duct walls 36 as shown in FIG. 3d. Hence, it is preferred that the gap distance should not exceed about one third of the length of the proximally adjacent bead.

Beads of the novel guidewire will also be defined by a characteristic length. By length is meant the maximum axial dimension of a bead, such as the dimension 20 in FIG. 1. The aspect ratio of beads, that is, the ratio of the length to the diameter, can also influence the ability of the distal potion to fold, kink or jam in the duct. Beads which have too great an aspect ratio will behave like long, rigid rods and will not be able to move through sharp curves. If the aspect ratio of the beads is too low, the beads may tend to bunch in a group to jam in the duct at bends and branch junctions. The physician should choose a guidewire populated with beads of size and spacing appropriately matched for the lumen to be probed. According to the present invention, the aspect ratio of the beads preferably should be within the range of about 0.75–2, and more preferably, about 1–1.5.

Although the beads for each guidewire shown in the figures are the same size, the beads of any particular guidewire distal portion can be different lengths, diameters and aspect ratios. Moreover, the gap distances between beads of a single distal portion can differ. Hence, the bead shape and spacing can be selected to provide a greater radius of curvature at the forward part of the distal end than at the trailing part.

Figure 4:
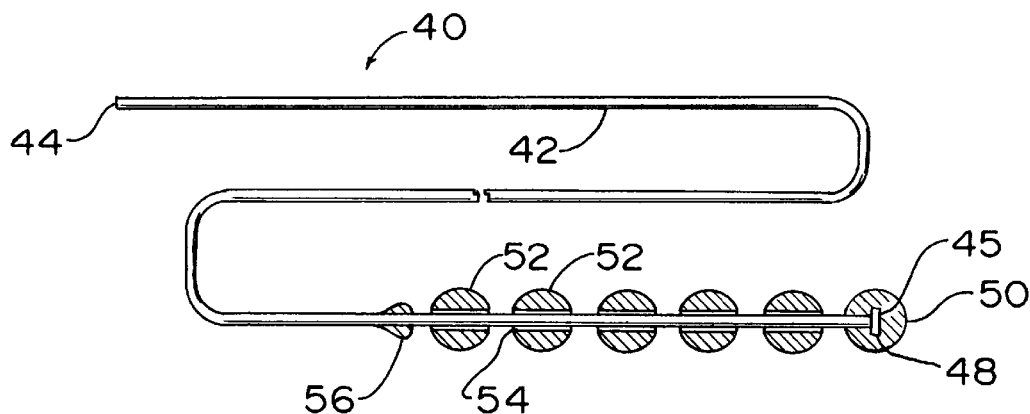
FIG. 4 is a partial section view of a guidewire according to the present invention wherein the beads slide freely along the distal portion of the core wire.

FIG. 4 illustrates a second specific embodiment of the invention in which the beads slide along the distal portion of the guidewire. Guidewire 40 includes a slender core wire 42 extending from proximal end 44 to tip 45 fixed to plate 48. Plate 48 is embedded within spherical head 50 so as to anchor the head to the core wire in a manner which prevents the head from accidentally detaching while the guidewire is within the body of the patient. The guidewire further includes a plurality of solid spherical beads 52 each of which is drilled through a meter to create a central bore 54. The bore diameter is larger than the diameter of the distal portion of the core wire which allows the beads to freely slide along the distal portion. Forward motion of the sliding beads is limited by the presence of the head which is a sufficient size to prevent the beads from falling off the distal end of the core wire. The core wire additionally includes a stop 56 fixed to the core wire between the proximal end and the most proximal sliding bead. The stop is defined by an enlarged cross section of sufficient size to prevent the beads from sliding toward the proximal portion of the guidewire. That is, the stop diameter is larger than the bore diameter. Hence, according to the illustrated embodiment of this invention, the beads can freely slide along the distal portion between the stop and the head. Such a guidewire advantageously can flex at many more locations along the distal portion than can the fixed bead embodiment shown in FIG. 1. This sliding bead embodiment thus is able to bend to a varying radius of curvature so as to automatically conform to duct bends which exhibit a wide range of curvatures. This guidewire should also be capable of threading through highly branched ducts having severely tortuous paths to the target site.

Figure 5:
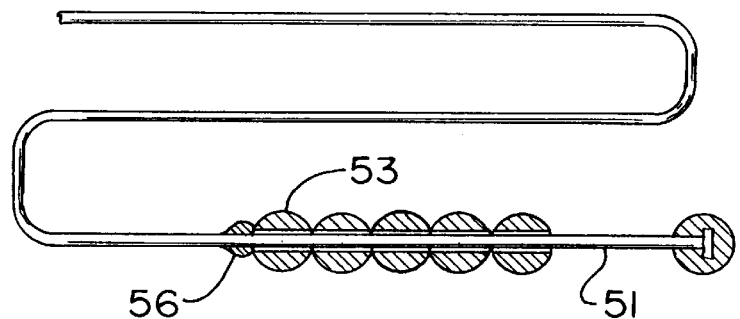
FIG. 5 is a partial section view of the guidewire of FIG. 4 wherein a long section of core wire extends beyond the beads.

When a duct is probed with a sliding bead guidewire, the beads generally will tend to drag until the most proximal bead 53 rests against the stop 56, as shown in FIG. 5. Alternatively, the beads can slide forward toward the head, for example when the head of the guidewire enters a steeply descending duct branch. In either of such circumstances, a long segment of the core wire 51 may extend beyond the central bores. This can substantially reduce the stiffness of distal portion. In order to maintain the adequate stiffness and to lessen the tendency for the distal portion to kink or jam, it is preferable to limit such extension to a maximum. Preferably, the overall length of the distal portion should not exceed the total bead length distance by more than about 30% and more preferably, by more than 10%. That is, the length of the core wire from the stop to the tip preferably should not be more than about 1.3, and more preferably 1.1 times the sum of all the bead lengths.

The sliding beads need not be solid. For example, the beads can be hollow with diametrically opposing apertures through which the core wire extends.

Figure 6:
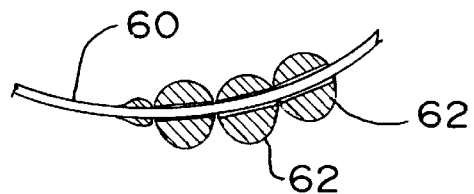
FIG. 6 is a section view of a part of the distal portion of a guidewire according to is invention wherein the bore through the beads is eccentric with respect to the diameter.

FIG. 6 illustrates a part of the distal portion of another contemplated embodiment. The core wire 60 passes eccentrically through the beads 62, i.e., not concentric with the bead diameter. Such alignment provides a natural curvature to the distal portion. It is customary for physicians to sometimes bend the tip of a conventional catheter guidewire prior to insertion in order to form a hook shape. Such bending allows the physician to direct the tip positioned at the threshold of a network branch by rotating the proximal end until the hook points into the lumen of the branch. The novel, beaded guidewire can be made to have a similar, slight, hook shaped curvature by passing the core wire through the beads eccentrically. In another contemplated variation of the illustrated embodiment, some of the beads are bored eccentrically and the remaining beads are bored concentrically with the diameter. This ability to form a natural hook shape at the distal portion by passing the core wire eccentrically through the beads can be employed in fixed bead as well as sliding bead guidewires.

Figure 7:
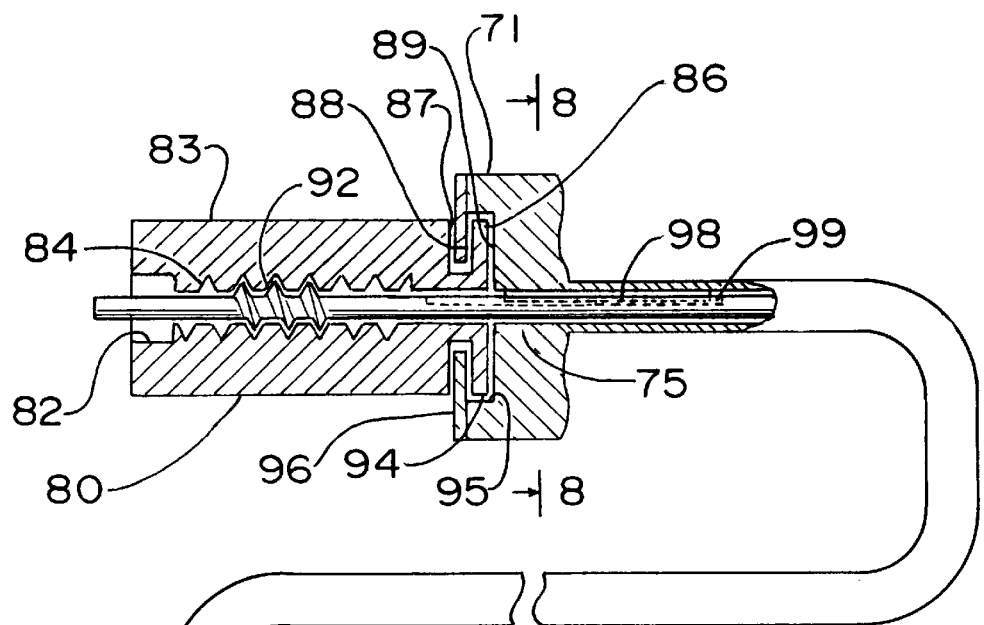
FIG. 7 is a section view of a guidewire according to the present invention having a tubular sleeve.

Another embodiment of the present invention which employs sliding beads is illustrated in FIG. 7. This embodiment provides the advantageous feature that the stiffness, and thus to some degree, the curvature of the distal portion within a remote branch of the duct can be controlled during guidewire deployment by manipulation of the proximal end. The guidewire includes a tubular sleeve 74 which has coaxial bore 76. The lumen of the coaxial bore is sufficiently larger than the diameter of the core wire 70 that the sleeve can slide freely along the core wire. At the far end 79 of the sleeve, the coaxial bore 77 of the sleeve is enlarged to the extent that the sleeve can axially slide over the stop 72 to contact the most proximal bead 52. The outer diameter of the sleeve at the far end is smaller than the bead diameter yet larger than the diameter of the bead bore 54. These dimensions are selected to assure that the sleeve is able to advance into the duct to approach the most proximal bead 52 and to present a contact surface 78 which can bias against the trailing end 57 of the most proximal bead. The sleeve should be shorter than the core wire length yet sufficiently long that the near end 75 of the sleeve extends outside the body when the sleeve is fully threaded on the core wire. In this manner, the proximal end of the core wire extends outside the body beyond the sleeve so that both core wire and sleeve can be manipulated independently by the physician.

Figure 8:
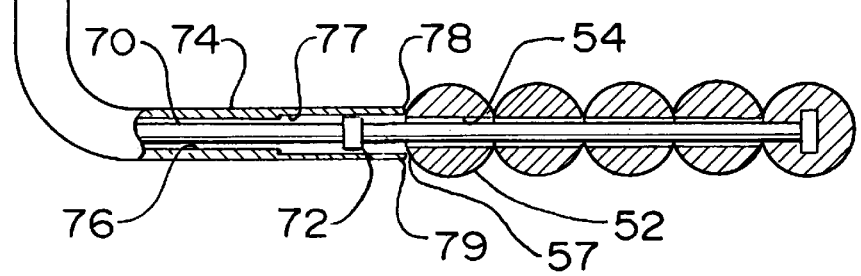
FIG. 8 is a section view of the guidewire of FIG. 7 viewed from line 8—8.
Figure 8:
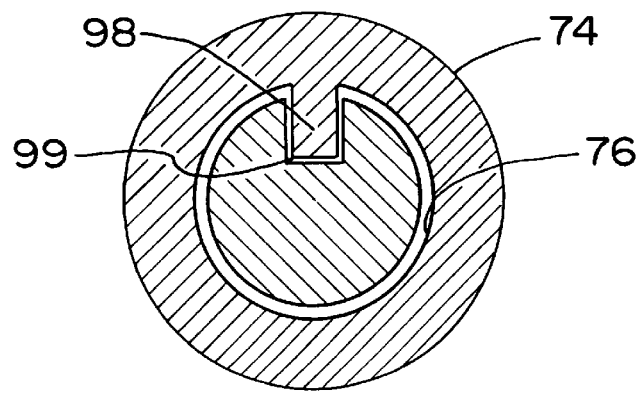

The guidewire optionally includes a means for controlling the relative axial positions of the sleeve and core wire. For example, the guidewire of FIG. 7 includes advancing nut 80 having a bore 82 with female screw threads 84 adapted to engage male screw threads 92 on the core wire near the proximal end. The advancing nut has an end flange 86 on the forward end of the nut which defines a circumferential groove 87 adjacent the nut body 83. The advancing nut mates with the near end of the sleeve insofar as the end flange 86 extends into cavity 94 formed by an enlarged diameter portion 95 of the sleeve 71 at the near end, thereby enabling the circumferential groove to receive a retaining ring 96 affixed to the near end of the sleeve. The retaining ring is held to the sleeve 71 by conventional fastening means, not shown, such as screws. The dimensions of the retaining ring and circumferential groove are selected to create close axial tolerance and sliding circumferential engagement between the retaining ring and advancing nut. Consequently, rotation of the advancing nut about the core wire causes axial movement of the nut induced by engagement of the screw threads to urge the end flange against near face 88 and far face 89 of the groove. The sleeve thus moves axially without rotating about the core wire. FIG. 8, showing a view through section 8—8 of FIG. 7, illustrates a key 98 extending radially inward from the coaxial bore of the sleeve. The key is adapted to engage a radial slot 99 near the proximal end of the core wire so as to further cause the sleeve to resist circumferential rotation as the advancing nut is turned. Hence, the sleeve can be advanced toward or drawn away from the core wire tip to a continuously adjustable extent by rotating the advancing nut in the appropriate direction.

The type of means for adjusting advancement of the sleeve is not critical. Other equivalent means for controlling relative axial position of the sleeve and core wire as are readily apparent to one of ordinary skill in the art in light of the instant disclosure are contemplated to fall within the scope of the present invention.

The novel catheter guidewire equipped with a tubular sleeve is used as follows. The guidewire is prepared for insertion by retracting the sleeve until the contact surface 78 is proximally distant from the stop 72. This relieves compression between the beads and makes the distal portion most flexible. Alternatively, the sleeve can be removed from the guidewire temporarily.

Next, the guidewire is inserted into, and urged forward in the duct toward the target site until it reaches a branch junction. If previously removed, the tubular sleeve can be re-installed by sliding the sleeve over the proximal end of the core wire and advancing the sleeve forward. From the proximal end the guidewire and sleeve together can be twisted and repeatedly pushed and pulled, in forward and reverse directions, so as to direct the head into the desired branch at the junction. Also, the patient's body can be rolled, inclined and otherwise oriented in such manner as to use gravity to move the guidewire head and the most distal beads into the proper duct branch. In addition, the physician can gradually move the sleeve forward on the core wire until the contact surface at the far end of the sleeve begins to bias against the most proximal bead. For guidewires equipped with an advancing nut mechanism, this can be accomplished by rotating the nut the appropriate direction. As the advancing nut is increasingly turned, the sleeve moves farther forward on the core wire. Advancing the sleeve pushes the beads forward on the distal end of the core wire to reduce the total gap distance between the beads. The reduction in gap distance increasingly limits the ability of the distal end to flex between beads, and thus, increases distal portion stiffness. The beads ultimately become compressed between the head and the contact surface of the sleeve thereby stiffening the distal portion to a maximum amount. The physician can advance or retract the sleeve slightly to increase or decrease the degree of distal portion stiffness by rotating or counterrotating the advancing nut. By exercising in concert all the tools of advancing and retracting the guidewire, adjusting distal portion stiffness and changing body orientation to varying degrees, the physician should be able to effectively, quickly, and without damaging the duct walls, steer the distal portion through a curve at the junction and into the desired duct branch.

Once the guidewire has successfully negotiated a curve at a duct junction, it can be pushed farther into the duct until the next junction is encountered. The sleeve can be retracted slightly relative to the core wire to reduce compression of the beads, and thereby increase distal portion flexibility. At the next junction, the distal portion again can be adjusted by advancing or retracting the sleeve on the core wire.

The beads and/or core wire can be made of radioopaque materials. Accordingly, conventional fluoroscopy techniques can be used to allow the physician to monitor the progress of the guidewire distal portion and to steer the guidewire into the proper branch at each duct junction.

The procedure of negotiating the guidewire into the desired branches of the duct at successive junctions is repeated until the guidewire tip arrives at the intended target site. If a tubular sleeve is used, it can be removed completely by sliding it off the proximal end of the core wire. A catheter then can be placed over the proximal end and threaded into the duct along the guidewire by conventional means. Finally with the catheter suitably deployed, the guidewire can be retracted from the duct, if necessary.

In another embodiment of the novel catheter guidewire shown in FIG. 9 the distal portion comprises a chain of a plurality of ball and post member segments. The ball members are spheroidal and the post members are elongated. Each segment includes a ball member 102 pivotably connected at a position 104 on the surface 103 to first post end 112 of a post member 110. The second post end 114 is linked to a neighboring segment with a pivotable connection to an adjacent ball member 120. The pivotable connection to the second post end is positioned on the surface 123 of the adjacent ball member diametrically opposite to the first post end 122 of the adjacent post member. The plurality of ball and post members thus form a sequential chain which may be likened to a common key chain or electrical fixture pull chain.

As stated, the chain of ball and post member segments forms the distal portion of the guidewire. One end of the chain is attached to the distal end 111 of the core wire 113. The most proximal ball member 102 can be attached so as to pivot around the distal end or it can be immovably attached. The free end 125 of the chain has a head 126 with a blunt forward end 127. The head can be a specially formed second post end. Preferably, the head is spheroidal ball member without a second post member connection position.

The method of effecting the pivotable connection between ball members and post members is not critical. A universal joint configuration similar to that of an automobile drive shaft, for example, is acceptable, however, a ball and socket joint is preferred. In order to incorporate such a ball and socket joint, the ball member can include at the pivotable connection position a convex, spherical cavity 107 to form the socket adapted to receive a spherical ball 115 affixed to the ends of the post member.

Another preferred embodiment of the novel guidewire having ball and post members is illustrated in FIG. 10. Each ball member is a hollow spheroid 130 having two diametrically opposite openings 132 and 134. The post member 140 has a cross section diameter smaller than the opening diameter which permits the post end 142 to extend into the openings so that the post member 140 slidably engages two adjacent ball members 130 and 136. The post ends 142 include a flange 143 having a cross section diameter greater than the opening diameter. The flange prevents the post end from disengaging from the ball member. In is embodiment, a clearance between the post member diameter and the lip of the opening allows the post member to pivot about the lip. In addition, this type of guidewire provides the beneficial feature that the post members can penetrate the ball members to varying extents. That is, the gap distance can range from zero when the intermediate post member between adjacent ball members is inserted wholly inside the adjacent balls, as shown in FIG. 11, to a maximum when the ball members extend to the limit of the intermediate post member and are constrained by the flanges as shown in FIG. 12. Therefore, this ball-and-post member construction distal portion, can conform to the curvature of the bodily duct extremely well.

Figure 13:
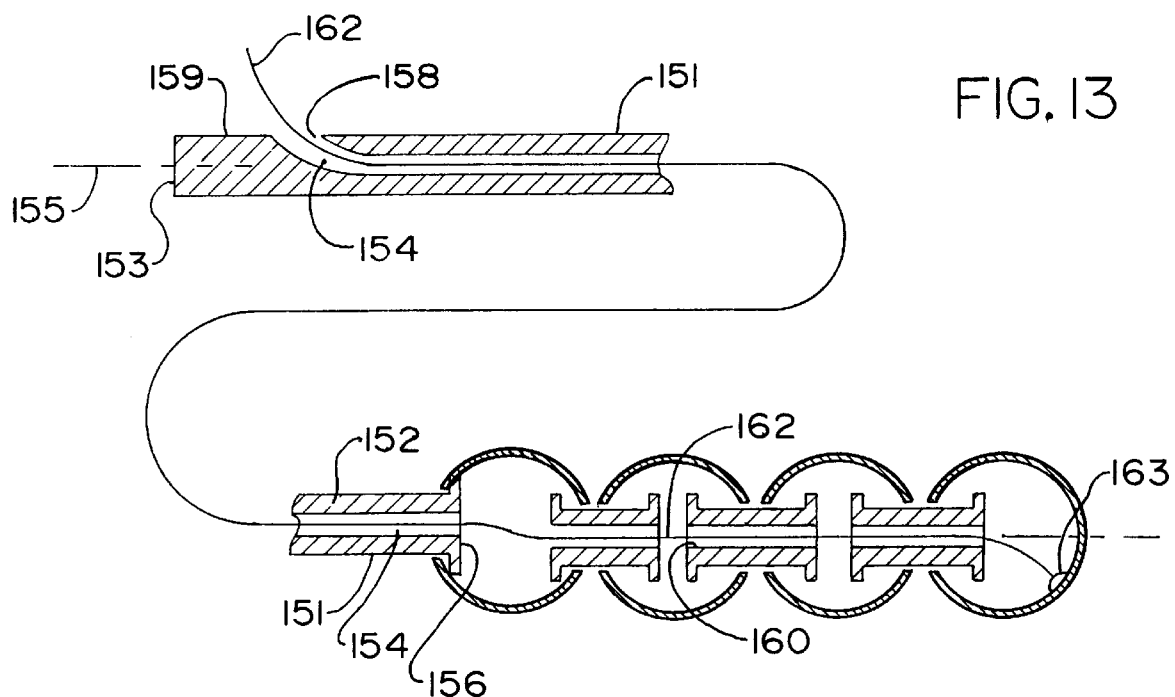
FIG. 13 is a section view of another embodiment of a ball and post member guidewire according to this invention.

A particularly preferred embodiment of the ball and post member novel guidewire is shown in FIG. 13. The proximal portion 151 of the core wire 152 has a central bore 154 extending from the distal end 156 to an exit orifice 158 near the proximal end 153. Near the proximal end, the bore can remain concentric with the longitudinal axis of the core wire to emerge at the proximal end, or it can veer away from the axis to emerge from the core wire at the circumferential surface, as shown. In addition, each post member is hollow to define a longitudinal tunnel 160 therein. One end of a line thread 162 is affixed to the distal end of the guidewire. The other, free end of the thread is lead back to the proximal end of the guidewire through each post member tunnel and ball member, and the central bore of core wire. The thread can be affixed internally to the distal end of the guidewire at any axial position, however, eccentric attachment at a position offset from the axis is preferred. Such eccentric attachment position permits the distal portion to form a curve when the thread is tensioned, as will be explained.

The thread is sufficiently long that the free end extends outside the body at the proximal end of the guidewire. By tensing the thread, the physician can pull the ball members proximally. This causes the post members to insert into the ball members, as described above, and the gap distances between ball members to diminish. Tensing the thread thus stiffens the distal portion. Accordingly, the physician can manipulate the stiffness of the distal portion to maximum advantage while deploying the guidewire into branches of the bodily duct by gently pulling and releasing the free end of the thread. FIG. 13 shows an advantage provided when the core wire central bore 154 veers away from the axis 155 to emerge from the core wire at the circumferential surface 159. Specifically, the free end of the thread extends from the guidewire at a position convenient for the physician to manipulate the thread with one hand while grasping the core wire near the proximal end with the other hand.

Fixed bead guidewires according to the present invention can be deployed in a manner similar to that described above. However, the physician will not have the ability to remotely adjust stiffness of a fixed bead guidewire distal portion during deployment.

Figure 14:
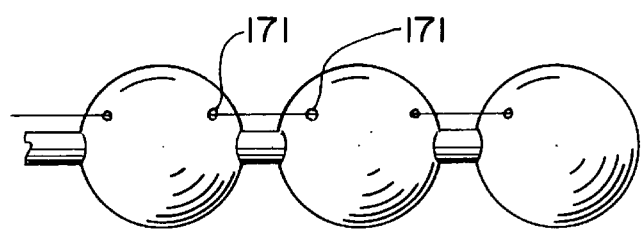
FIG. 14 is a side view of a part of the distal portion of a ball and post member guidewire according to the present invention wherein a thread extends through holes in the ball surfaces.

Variations of ball-and-post member embodiments of the novel guidewire which can induce curvature in the distal portion are contemplated. For example, the two openings for posts in each ball member can be eccentric from the diameter, i.e., so that the openings are not diametrically opposite each other. Consequently, when the posts insert into the balls as can occur when the distal portion encounters the wall at a duct junction, the distal portion will form a hook shape, as has been described above. Also, the thread end 163 can be affixed to the distal end of the guidewire offset from the guidewire axis 155, as illustrated in FIG. 13. Alternatively, the thread can be run externally to the posts by penetrating the ball members through holes 171 provided as shown in FIG. 14. In such embodiments tensioning the thread will induce curvature in the distal portion, much in the way that a human finger deflects from an initially straight orientation to grip a curved object when the digital muscles are contracted.

Figure 15:
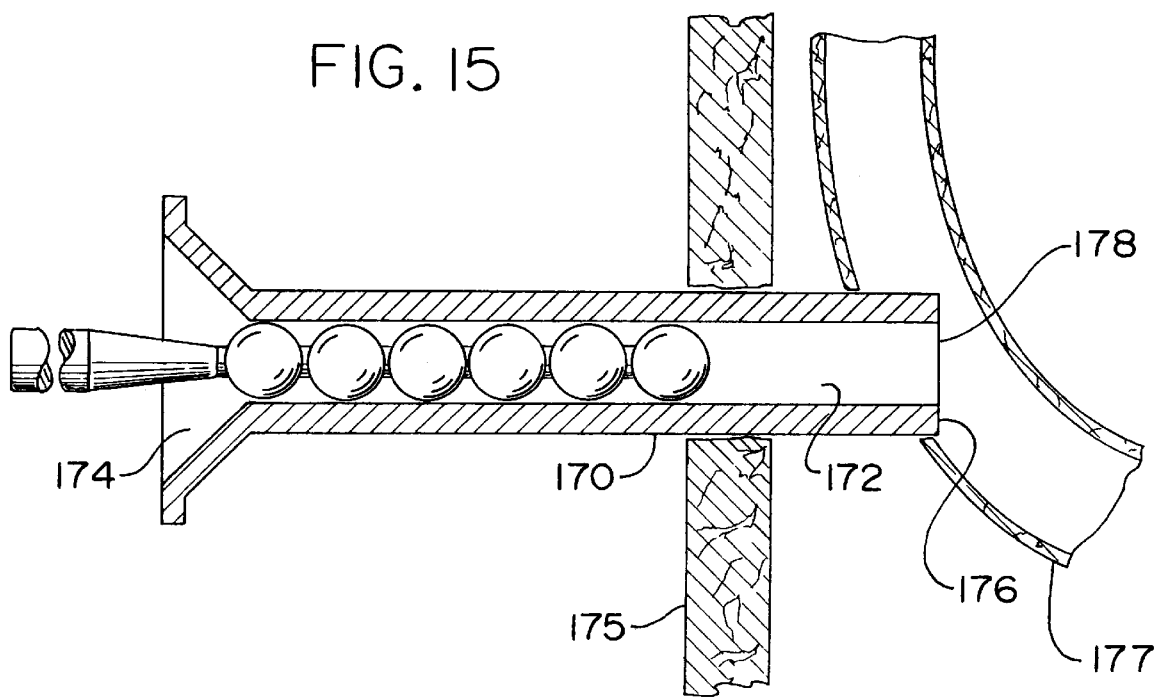
FIG. 15 is a section view of an insertion tube inserted into a bodily duct.
Figure 16:
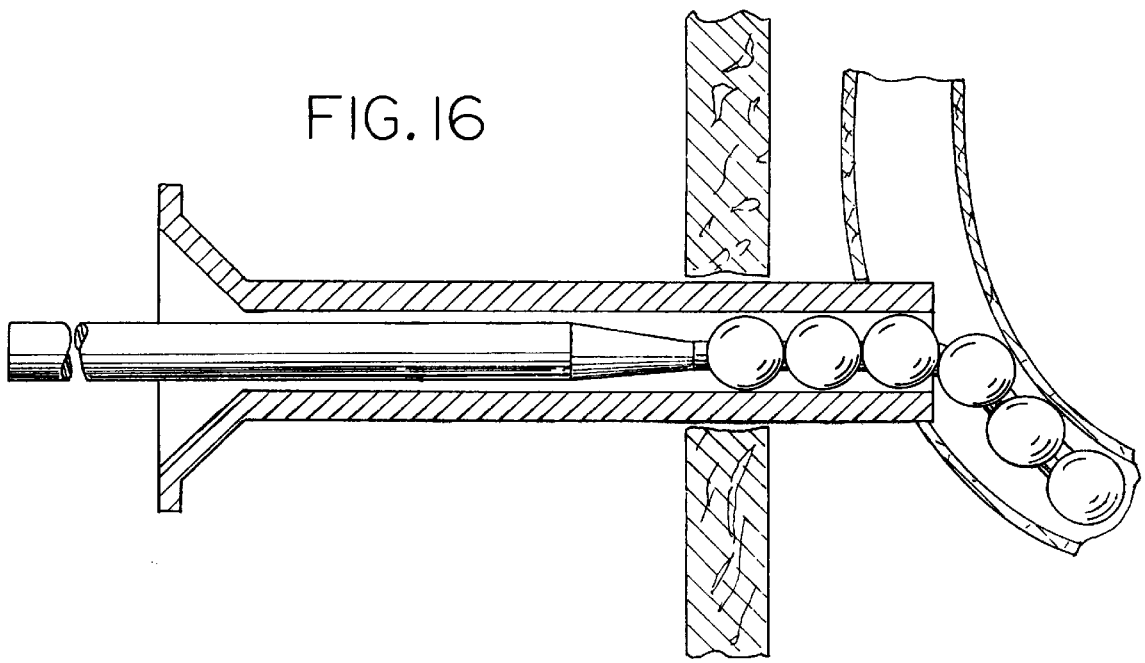
FIG. 16 is a section view of the insertion tube of FIG. 15 showing the leading beads of the guidewire feeding into the bodily duct.

The distal portion of the novel guidewire will be in a most flexible state for example when the sleeve is retracted or removed, or the thread is completely untensioned. In such condition, it may be difficult to initially feed the distal portion into the duct at the incision point, as by analogy, it is sometimes hard to thread a limp fiber through the eye of a needle. In order to facilitate feeding the extremely flexible distal portion into the duct while maintaining the beads aligned in single file behind the head, the present invention can include an optional insertion tube 170 as shown in FIG. 15. The insertion tube is basically a rigid, hollow cylinder with a tube lumen 172 having a diameter slightly larger than the bead diameter, and preferably less than two bead diameters. The insertion tube preferably has a funnel-shaped proximal orifice 174. In use, the distal extremity 176 of the insertion tube is injected through the skin 175 and past subdermal tissue, not shown, into the duct 177. Outside the body, the distal portion of the guidewire is easily fed into the funnel-shaped proximal orifice and advanced within the tube lumen. The distal portion of the guidewire is then urged forward into the insertion tube. Owing to the small tube lumen diameter, the beads remain in single file while traveling the full length of the insertion tube. Finally, the head and trailing beads emerge from the port 178 at the distal extremity inside the body duct in single file alignment as shown in FIG. 16. Length of the insertion tube is not critical. Preferably, the overall length of the insertion tube is about 2 to about 20 cm. After the distal portion of the guidewire fully enters the duct, the insertion tube can be removed from the proximal end of the core wire.

The catheter guidewire of the present invention should be useful for deploying catheters in fluid filled cavities such as the dural sac. For example, it can be used to probe along the spinal cord by access through a lumbar puncture. In such fluid filed applications, materials of densities substantially different from the fluid density can be used to make beads which will float or sink in the fluid. Buoyant or sinking beads can help direct the guidewire up or down toward the target site. Preferably, the beads should have a density significantly greater or less than 1 g/cm$^3$, and more preferably, higher than 1.2 g/cm$^3$ and lower than 0.8 g/cm$^3$. Low density plastics or gas-filled beads can be used for light beads and metal can be selected for high density beads.

The novel catheter guidewire of this invention can be constructed from conventional materials well known in the art, such as metal or plastic. Metal beads of titanium and stainless steel, for example, will be radioopaque, and therefore, are preferred. The tubular sleeve can be constructed of synthetic elastomer. Metal wire or plastic such as nylon can be used for the tensioning thread.

I claim:

1. A catheter guidewire having a leading end, the guidewire comprising:

a core wire adapted to insert into the lumen of a duct of a body, the core wire having a proximal end adapted to remain outside the body, a distal end, and a core diameter; and a beaded portion appended to the distal end forming the leading end of the guidewire, the beaded portion comprising a plurality of spheroidal beads sequentially disposed along the core wire each bead having a bead length in a direction axial to the core wire and wherein adjacent beads are axially spaced apart by a gap distance; and a blunt forward end.

2. The catheter guidewire of claim 1 wherein the beads have a bead diameter sufficiently small for the core wire to move freely through the lumen and an aspect ratio of bead length to bead diameter of about 0.75 to about 2.

3. The catheter guidewire of claim 2 wherein the beads are affixed to the core wire and the gap distance is at most one third of the bead length of the bead proximally adjacent the gap distance.

4. The catheter guidewire of claim 2 wherein the core wire extends through a central bore in each bead, the central bore defined by a bore diameter that is sufficiently larger than the core diameter to permit the beads to slide freely along the distal portion.

5. The catheter guidewire of claim 4 wherein the core wire further includes a stop having a stop diameter larger than the bore diameter and wherein the stop is affixed to the core wire proximal of the beads.

6. The catheter guidewire of claim 5 wherein the stop is distant from the forward end by at most about 1.3 times the sum of all the bead lengths.

7. The catheter guidewire of claim 4 further including adjustment means for remotely controlling stiffness of the distal portion from the proximal end.

8. The catheter guidewire of claim 7 wherein the adjustment means comprises a radially flexible, longitudinally incompressible, tubular sleeve having a sleeve lumen larger than the core diameter and an outer sleeve cross section larger than the bore diameter, the tubular sleeve being adapted to freely slide over catheter guidewire from the proximal end and to contact the most proximal bead with an axial force applied from the proximal end effective to compress the beads between the head and the sleeve thereby stiffening the distal portion to a desired extent.

9. The catheter guidewire of claim 8 wherein the adjustment means further comprises at least one thread affixed at one thread end eccentrically to the tip and extending through the central bore of each bead and through the sleeve lumen to the proximal end.

10. The catheter guidewire of claim 2 wherein the beads are spheres.

11. The catheter guidewire of claim 2 wherein the beads have a density significantly greater than or less than 1 g/cm$^3$.

12. The catheter guidewire of claim 2 wherein the guidewire further includes a removable, rigid, hollow insertion tube comprising a funnel-shaped proximal orifice, a port distant from the proximal orifice, and a tube lumen slightly larger than the bead diameter being adapted to slide over the core wire to feed the beads through the port in axial alignment into the lumen of the bodily duct.

13. The catheter guidewire of claim 11 wherein the density of the beads is outside the range from about 0.8 g/cm$^3$ to about 1.2 g/cm$^3$.

14. A catheter guidewire adapted to insert into the lumen of a bodily duct comprising:

a core wire having a distal end;

a distal portion attached to the distal end of the core wire including a plurality of segments, each segment including a spheroidal ball member pivotably and slidably connected to a post member, wherein the post member of each segment is pivotably and slidably connected to the ball member of an adjacent segment in sequence to form a chain of segments having a free end; and a head at the free end of the chain that has a blunt forward end.

15. The catheter guidewire of claim 14 wherein the core wire has a central bore wherein each segment includes a hollow, spheroidal ball member having two diametrically opposite openings and a post member having a post cross section smaller than the openings and two post ends, wherein one post end extends through one of the two openings into the ball member so that the post member slidably engages the ball member and wherein the second post end extends inside the second of the two openings into the ball member of an adjacent segment, and wherein each post end includes a flange defining a flange cross section larger than the opening, thereby preventing the post member from disengaging from adjacent ball members; and a head at the free end of the chain having a blunt forward end.

16. The catheter guidewire of claim 14 which further comprises at least one thread affixed at one thread end eccentrically to the head and running externally to the post members through penetration holes of the ball members.

\* \* \* \* \*

UNITED STATES PATENT AND TRADEMARK OFFICE
CERTIFICATE OF CORRECTION

PATENT NO. : 5,902,254
DATED : May 11, 1999
INVENTOR(S) : Gary Magram

It is certified that error appears in the above-identified patent and that said Letters Patent is hereby corrected as shown below:   On title page, Section 54: Delete "H" after 2nd T in CATHETER
 Col. 1, line 1,
      Delete "H" after 2nd T in CATHETER Col. 1, Line 16: Delete "("PITCA") after the word angioplasty and insert --("PTCA")--.
Col. 1, Line 45: Delete "cam" after the word catheter and insert --can--.
Col. 4, Line 17: Delete "elate" after the word to and insert --eliminate--.
Col. 5, Line 13: Delete "trading" after the word the and insert --trailing--.
Col. 5, Line 21: Delete "ache" after the word contact and insert --each--.
Col. 8, Line 11: Insert --in-- after the word nut.

Signed and Sealed this

Seventh Day of September, 1999

Q. TODD DICKINSON

Attest:

Attesting Officer

Acting Commissioner of Patents and Trademarks